(12) United States Patent
Shuck

(10) Patent No.: US 8,491,495 B1
(45) Date of Patent: Jul. 23, 2013

(54) HUMAN INTESTINAL TRACT RESEARCH AND DIAGNOSTIC SYSTEM TO EVALUATE PATIENTS AND ADVANCE MEDICAL SCIENCE AND BIOENGINEERING AND TO DETERMINE PROCESSES IN THE GUT AND CAUSES OF DISEASES

(71) Applicant: L. Zane Shuck, Morgantown, WV (US)

(72) Inventor: L. Zane Shuck, Morgantown, WV (US)

( * ) Notice: Subject to any disclaimer, the term of this patent is extended or adjusted under 35 U.S.C. 154(b) by 0 days.

(21) Appl. No.: 13/691,169

(22) Filed: Nov. 30, 2012

Related U.S. Application Data

(60) Provisional application No. 61/727,177, filed on Nov. 16, 2012.

(51) Int. Cl.
*A61B 10/02* (2006.01)

(52) U.S. Cl.
USPC .......................................................... 600/562

(58) Field of Classification Search
USPC .......................................................... 600/562
See application file for complete search history.

(56) References Cited

U.S. PATENT DOCUMENTS

| | | | | |
|---|---|---|---|---|
| 2,881,756 A | * | 4/1959 | Crosby et al. .................. | 600/565 |
| 3,057,344 A | * | 10/1962 | Abella et al. ................... | 600/582 |
| 3,118,439 A | * | 1/1964 | Perrenoud ...................... | 600/582 |
| 3,485,235 A | * | 12/1969 | Felson ........................... | 600/582 |
| 3,528,429 A | * | 9/1970 | Beal et al. ...................... | 600/367 |
| 3,683,890 A | * | 8/1972 | Beal ............................... | 600/371 |
| 3,688,763 A | * | 9/1972 | Cromarty et al. .............. | 600/572 |
| 4,036,214 A | * | 7/1977 | Bucalo ........................... | 600/582 |
| 5,170,801 A | * | 12/1992 | Casper et al. .................. | 600/582 |
| 5,971,942 A | * | 10/1999 | Gu et al. ........................ | 600/582 |
| 7,449,001 B2 | * | 11/2008 | Stoltz ............................. | 600/582 |
| 7,452,338 B2 | * | 11/2008 | Taniguchi ...................... | 600/593 |
| 7,611,480 B2 | * | 11/2009 | Levy .............................. | 604/27 |
| 7,686,770 B2 | * | 3/2010 | Cohen ........................... | 600/568 |
| 7,717,862 B2 | * | 5/2010 | Stoltz ............................. | 600/582 |
| 7,740,595 B2 | * | 6/2010 | Brown ........................... | 600/565 |
| 7,938,775 B2 | * | 5/2011 | Rabinovitz et al. ........... | 600/309 |
| 8,195,276 B2 | * | 6/2012 | Uchiyama et al. ............. | 600/424 |
| 8,343,069 B2 | * | 1/2013 | Uchiyama et al. ............. | 600/562 |
| 8,394,034 B2 | * | 3/2013 | Iddan et al. .................... | 600/582 |
| 8,406,490 B2 | * | 3/2013 | Gat et al. ....................... | 382/128 |
| 2001/0051766 A1 | * | 12/2001 | Gazdzinski ..................... | 600/309 |
| 2002/0042562 A1 | * | 4/2002 | Meron et al. ................... | 600/361 |
| 2002/0103417 A1 | * | 8/2002 | Gazdzinski ..................... | 600/109 |
| 2002/0132226 A1 | * | 9/2002 | Nair et al. ......................... | 435/4 |
| 2003/0020810 A1 | * | 1/2003 | Takizawa et al. ................ | 348/68 |
| 2003/0085994 A1 | * | 5/2003 | Fujita et al. ...................... | 348/77 |
| 2003/0181788 A1 | * | 9/2003 | Yokoi et al. ................... | 600/160 |
| 2003/0213495 A1 | * | 11/2003 | Fujita et al. ................... | 128/899 |
| 2004/0092825 A1 | * | 5/2004 | Madar et al. .................. | 600/473 |
| 2004/0115877 A1 | * | 6/2004 | Iddan ............................. | 438/200 |
| 2004/0122315 A1 | * | 6/2004 | Krill .............................. | 600/437 |
| 2005/0177069 A1 | * | 8/2005 | Takizawa et al. .............. | 600/573 |
| 2007/0173738 A1 | * | 7/2007 | Stoltz ............................. | 600/582 |
| 2008/0208077 A1 | * | 8/2008 | Iddan et al. .................... | 600/582 |
| 2009/0143697 A1 | * | 6/2009 | Tanaka .......................... | 600/565 |
| 2009/0253999 A1 | * | 10/2009 | Aoki et al. ..................... | 600/565 |

FOREIGN PATENT DOCUMENTS

JP              05168639 A    *    7/1993

* cited by examiner

*Primary Examiner* — Sean P Dougherty
*Assistant Examiner* — Michael C Stout

(57) ABSTRACT

Many diseases with origin in human gut are of unknown causes, so only symptoms are treated. Endoscopic devices leave about 15' of gut unexplored other than by autopsy. Thus, a substance and microbe simultaneous sample collecting, testing, evaluation, and characterization system has been invented that will provide data for evaluating functions, macro, and micro processes taking place along entire length of the human digestive and intestinal tract from mouth to anus. The entire digestive process including biochemical reactions and microbe roles, and consequences, as pertain to diseases and illnesses can be ascertained through applications of the system, which includes protocols, for collection and preservation of digestion products for external analysis, measurements of many in vivo conditions, and internally processing data and making decisions based upon said processed data, including administration of medications. The system serves clinical diagnostic, treatment and research purposes, and is a dream tool for gastroenterologists.

11 Claims, No Drawings

HUMAN INTESTINAL TRACT RESEARCH AND DIAGNOSTIC SYSTEM TO EVALUATE PATIENTS AND ADVANCE MEDICAL SCIENCE AND BIOENGINEERING AND TO DETERMINE PROCESSES IN THE GUT AND CAUSES OF DISEASES

The current application claims a priority to the U.S. Provisional Patent application Ser. No. 61/727,177 filed on Nov. 16, 2012.

FIELD OF THE INVENTION

The subject invention is a biomedical, bioengineering system, methodology, and protocol for analyzing the biological microbial colonization and biochemical endogenous processes in the human gut. These processes are believed to hold the secrets to the CAUSES of many diseases, of which are currently unknown, and only their symptoms are treated by physicians. This invention is intended to advance the fields of gut endocrinology, endoscopy, and microbiology by extending the endoscopic type tools available for not only visually inspecting sections of the gut, but simultaneously obtaining simultaneous biochemical and microbe samples in conjunction with a comprehensive sample gathering and handling system, instrumentation data acquisition, reduction, analysis, display, and modeling system, all uniquely and integrally designed based upon the new capability of in-vivo sampling from beginning to end of the human gut.

BACKGROUND OF THE INVENTION

Medicine has advanced in all major human body systems, such as cardiovascular, neurological, muscular and skeleton, but the intestinal tract still remains much of a mystery. The remote and inaccessible 15' sections of intestines, beyond the 6 feet up and 6 feet down as viewed by endoscopy/colonoscopy instruments, remain unexplored in live humans. Even these upper and lower extremities are viewed by camera and can only be treated for visible damage, such as polyps or ulcers. The roles bacteria play in the intestinal tract are generally not understood, except that there are "good" and "bad" bacteria. In fact, only a few of the estimated 1,000 to 2,000 strains of bacteria are known, or have been identified, much less characterized and their roles determined. Quantitative in-vivo data and measurements are generally not available, so science and engineering technology are largely stymied. The only major exception is that a camera pill can now be swallowed and pictures taken throughout the intestinal tract after being totally cleansed. The resulting information gleaned is largely qualitative. It is truly unfortunate that the scientific and medical research community has been remiss in developing such technology, which has led to serious consequences in medical treatments and costs to society.

In order to understand the CAUSES of up to 100 or more diseases and illnesses believed to be originating somewhere within the entire human intestinal tract, basic science and engineering data are necessary to analyze the biochemical, biological/physiological, and bioengineering processes taking place therein, along with the flora of microbes and the role they play in the digestive and other involved processes. Currently, in most gut-related diseases, only the symptoms are being treated under a wide variety of named diseases, Celiac being an example, while the causes remain unknown. In order to advance the medical science, bioengineering and technology to the same levels of DNA, microbiology in general, etc., as in other anatomical systems, sufficient in-vivo data must be available to develop intrinsic models and identify physiological processes, as opposed to superficial and grossly inferior statistical inference methods.

Specifically, what is not known within the human gut is a huge void in medical science!

1. The biochemical products existing for any specific diet are not known as a function of the gut length x.
2. The biochemical reactions taking place along the gut are not known as a function of the gut length x.
3. The microbes existing at any point within the gut anatomical system are generally unknown and unidentified.
4. The byproducts of all microbes existing within the gut are likewise unknown, much less as a function of x.
5. The aerobic/anaerobic distribution and associated conditions are vaguely known, but not as a function of x.
6. The interaction of a) the normal biochemical reactions, b) the microbes, and c) the microbe byproducts are totally unknown, and believed to be a major source of several major diseases.
7. The data necessary to identify and characterize physiological, biochemical or other bio-engineering processes, or construct any sort of a scientific, mathematical or engineering model of any component of the gastrointestinal system ranging from the stomach, duodenum, jejunum and ileum, through the colon are totally unavailable for healthy individuals as a function of x, much less for unhealthy individuals.
8. Some 15 categories of bacteria have been broadly identified within the Phylogenic Tree as existing within major components of the gastrointestinal tract. The microbial flora distribution for the gastrointestinal tract has been broadly cataloged for major components of the system, and general aerobe and anaerobe distributions and populations are broadly known for major components in healthy people, but not as a function of x, much less for people with diseases. More importantly, what about those new or previously undiscovered, or unidentified and uncharacterized strains that may be contributing to diseases? Thus, in general, bacteria strains and colonies and their populations, population densities, habitats, and characteristics and contributions to the digestive process are only very vaguely known in healthy individuals, and largely unknown in unhealthy individuals, much less as a function of x.
9. The characteristics of some bacteroides, individually, or in serial, or parallel, in conjunction with others and their independent diets and by-products in conjunction with the human digestive processes are generally unknown, much less as a function of x. (In this author's opinion, herein reside many explanations for malfunctioning of the human gut and sources of diseases.)
10. Additional critical information needed includes the ratios of solids, liquids, and gases, as well as, their compositions, temperature, partial pressures, and other variables. These quantities and variables are totally unknown in the intestinal tract, for any specific diet, especially for unhealthy individuals, much less as a function of x.

In summary, this perhaps represents only the top 10 priorities, and the beginning of information needed. The real summation effect of this huge void of scientific knowledge of the human gut is that the real origins and causes of many major human diseases are not known, and will not be known until such time as this above information is generated. While the general distribution of microorganisms within the gut of healthy humans is categorically mapped, such distribution in unhealthy people remains a mystery and there are no real diagnostic tools to investigate at the required levels and in an appropriate manner. There are many reasons why the human gut is largely unexplored, except for post mortem autopsies, which do not reflect much of the most important living dynamic phenomena and conditions. Meanwhile, medical treatments of symptoms of major diseases and illnesses, based upon hypothetical or worse, biased statistical data, form the basis of thousands of medications, and unnecessarily occupy valuable time of many medical professionals and clinics at a great cost to our Nation, which could otherwise be focused on permanent cures based upon causes instead of symptoms.

This invention is intended to provide for the first time, this and much more enabling science and engineering data and information, that can lead to revolutionary improvements in general health care. In testimony for the need for this information, the author of this invention is also the discoverer of the cause based process of a class of diseases known as Celiac or in general "gluten sensitivities", which he believes is the basis for many other major diseases. The above information is also necessary to provide absolute proof of his discovery, which is what led to this invention 1½ years ago.

SUMMARY OF THE INVENTION

The subject invention includes a comprehensive process, methodology, mechanical devices, protocols, and computer-based data acquisition, reduction, analysis, display, and modeling hardware and software system for gathering and extracting in-vivo biological specimens from beginning to end of the human gut and digestive system. Features and functions include preserving the sample's in-vivo environmental integrity, conducting sample chemical analyses, microbe strains/colonies identification and characterization along the entire intestinal tract, compiling and analyzing the data, displaying it in real time retroactively using 3-D computer graphics simulations as it was obtained, which will allow construction of mathematical, physiological, biochemical, and other engineering models, and delineation of causes of diseases originating within the gut. This quick-response system will also provide immediate patient data for attending physicians to assess and classify damages and diseases, immediately prescribe diets or medications, and equally important, provide physicians, when a second patient testing and evaluation is conducted, with fast quantitative results as to the effectiveness of prescribed diets and medications in a matter of 2 or 3 weeks, as opposed to waiting for months to see if treatments are working in any visible or statistically significant, or other largely qualitative evaluation manner. The entire process will eliminate much of the inferior statistical methods of testing large populations over extended periods of years to correlate symptoms and cause/effect relationships as to causes of diseases. In contrast, this invention can result in development of intrinsic models based upon basic principles of science and engineering at the molecular and microbe, as well as, macro levels. As a result, the various fields in the micro world, such as microbiology, can be merged with those scientific and engineering fields in the macro world to integrate and create more holistic understandings of the involved processes within the all important human gut, and then appropriate cures for many major diseases should occur.

DETAILED DESCRIPTIONS OF THE INVENTION

A comprehensive Research and Diagnostic System is invented and designed that consists of the necessary components to acquire, store, and preserve intestinal samples in in-vivo conditions, including during such time as comprehensive testing, analysis and characterization of the matter consisting of both inanimate substances and microbes, as existed in-vivo at the exact same location and time, as a function of the length of the entire intestinal tract, is performed. The methods, processes, apparatuses, research procedures, and patient application protocols are all part of said invention, which constitutes an entirely new technology for patient diagnostics, and advancement of scientific and engineering knowledge of the human gut.

The Research and Diagnostic System (RDS) consists of a Pill or Capsule that can be swallowed along with any typical, patient preferred diet, or a research designed and prescribed diet, and/or a prescribed total protocol. The Capsule acquires samples of matter continuously along the entire intestinal tract and stores and preserves it in "in-vivo" conditions until it can be inserted into the Incubator and Manipulator, and subsequently the Analyzer. The Capsule can also deliver said samples to any other laboratory instruments capable of testing said samples for any known variable or reason, or even frozen and used in future to-be-determined tests.

The Incubator and Manipulator functions to preserve the environment in which samples were obtained and transfer said samples into other storage or testing apparatuses.

The Analyzer is a work station of multiple testing equipment and apparatuses that have been specifically designed, or selected and modified, with specific probes designed to interface with the samples containment vessel, (as exemplified only as an example, the thin film encapsulated belt of samples) and perform a large variety of chemical, physical, microbial, materials, and other tests to determine their compositions, basis and origins of formation, genetic makeup, and numerous other characterizations. The Analyzer consists of chemical and physical probes and a variety of spectrometers and microscope devices, chemostats, that in combination can perform chemical and biological tests to identify chemical compositions and characteristics of the matter, and identify and characterize microbes, their population densities, aerobes and anaerobes, all of which exist and are sampled simultaneously along the entire intestinal tract as a function of length x. It should be noted that, depending upon the specific purpose of investigation and use of the RDS or specific protocol, not every sample will need to be tested by all of the equipment and apparatuses contained at the Analyzer work station, as a means of reducing total cost and time for obtaining the specifically desired information.

The final component of the RDS is a laboratory Computer-Based Data Acquisition, Reduction, Analysis, and Display System (CBDARADS). This system consists of conventional computer-based hardware and software modified and programmed to acquire all raw data from the Analyzer, or other sources of data and information resulting from tests on the subject samples, or other scientific data available from any source, and process said data involving all phases of data reduction, conversion, analysis, interpretation, and automatically displaying it in various forms of computer, and computer animated graphics, including 3-D. Many software subroutines are written to make calculations utilizing said data, and presenting it in meaningful formats to specialists for easy and fast interpretation.

It is important to note that at this point of discussion, and for simplicity and clarity of describing this invention, the Capsule has been described briefly above as a passive sample gathering apparatus, wherein all testing of the samples collected as a function of x is performed, and data are stored in bench-top elaborate, sophisticated laboratory instruments of substantial size and space requirements. This distinction is made for a host of reasons. First and foremost is because the system described to this point can be fabricated and implemented immediately without futuristic, miniaturized, instrumentation development. The Capsule described up to this point will now be delineated as Capsule A, because it is a passive sample intake form of sample collector, wherein no electronics, measurements, tests, instrumentation, or data acquisition are made or contained therein.

In contrast, there is also Capsule B included as part of this invention, where internal and external capsule measurements are made by sensors and transducers mounted on the surface, as well as internally, within the capsule to make real time measurements, store the data, and simultaneously transmit it externally from the human body in real time. At the present state of technology development, this Capsule B as herein defined is extremely limited in capability. However, part of the objectives of this invention is to initiate or trigger a suitable in vivo miniaturized instrumentation and data acquisition/transmission development revolution for better and immediate patient internal diagnoses and rapid development of in-the-gut technology. Measurements presently included in Capsule B are temperature-differences referenced to body temperature in the mouth, pressure differences/fluctuations along with pulse, pH, perhaps $O_2$, and hopefully, other gas component compounds of hydrogen and sulfur. Capsule B, with on-board electronics, is also capable of releasing or injecting stored substances, ranging from medications at some given instant, or dyes, for example. In this regard, this invention disclosure is also a call for others of all disciplines for R & D of in vivo capsule compatible sensors and transducers. Likewise, this patent disclosure author also anticipates filing new separate invention disclosures for such instrumentation. It should be noted that this invention also includes the method and process of integrating Capsule A and Capsule B functions into one capsule as the technology is advanced.

RDS Components, Methods, and Applications
Detailed Descriptions

1. Capsule A

The Capsule performs a number of distinct functions. First, it collects simultaneously partially digested biochemical products and microbes existing simultaneously at every desired point along the intestinal tract. Second, it encapsulates said samples and preserves them in a sealed environment ready for transfer, using the Incubator and Manipulator, to the Analyzer for examination and testing by the probes in it, or by other instruments in any other laboratory. The samples are taken at any pre-determined, programmable rate or frequency, and the time is recorded as the Capsule passes through the intestinal tract, which may be typically from a couple to 30 hours. The progress and exact position of the Capsule can be monitored and tracked, as a function also of time, by various remote sensing methods such as x-ray or MRI, or active telemetry from the Capsule accompanied by a receiver worn on a belt. As one particular design of Capsule A, called, Capsule $A_1$, for now, samples are collected and stored by a wafer battery-powered motor driven thin, sterile, ribbon-belt of pre-designed length, which contains indent pockets of various prescribed volumes, and shapes spaced in pre-designed patterns to accommodate sampling frequency and total number of samples quantity. As each sample is obtained, a sealant layer of sterile film is pressed against the belt to encapsulate the sample and separate it from matter down stream, and preserve the entire environment under which it was obtained. The motor speed can be set according to the apriori designed protocol prior to ingestion. The indent pockets shapes and sizes are pre-designed to accommodate a variety of microscopic methods and instruments, and designed test objectives and methods, so the samples are ready for both microbiological and chemical analysis. Each light wave opaque shell or housing of the Capsule, and internal cartridges, and sample belts and tubes also have unique serial numbers. The ends of the capsule are attached by fine machined threads and sealed with miniature O-rings in such manner for ease of assembly of motor, battery, and sample film indexed belts, spools and drive-train cartridge. The curvature of the ends of the Capsule is also of prescribed algebraic equations with three basic designs: a) to accelerate with minimum energy passage of Capsule through the intestinal tract and thrust it against intestinal wall, b) to accommodate sampling on a radial basis across the circular/elliptical cross section of the intestine, as opposed to the normal longitudinal sampling up against the wall of the intestine, and c) to provide a maximum energy or drag of flow through the intestine matter, such that the Capsule only progresses with the normal progression of the digested products. The lengths, diameters, and shapes of the Capsules are also designed within the various intestine system constraints, such as intestine folds and the sphincter muscle. The spooling-indexing means incorporates multiple drive, tensioned take-up and idler spools mounted in a cartridge with forward/reverse spooling capability. The cartridge also includes the spools of sample hermetically sealing thin film that is permanently attached to the sample collection belt as it is deployed and samples collected. A fine mesh grille attached to the capsule housing separates and prevents the sample collecting belt from touching the lining, epithelium, villi, or obtrusive parts of the intestines. The two spools for sample film storage can also be removed from the capsule sample acquiring cartridge and placed robotically or manually into another storage capsule, or a Reader-Analyzer cartridge with a similar indexing drive motor that allows for variable spacing between dispensing and take-up spools, and x-y traverse by micro indexing table for sample automated testing or placing on various microscopic examination attachments. In this manner each indexed sample pocket can be individually tested, manually or automated, using various wavelength spectrographic or SEM, or numerous other microscopic means, including, for example, pattern recognition and microbe behavior hardware/software technology.

2. Capsule B

There is no allusion that many essential tests and analyses as described below in the Analyzer and CBDARADS can ever be adequately incorporated within an in vivo ingested capsule. However, Capsule B not only incorporates currently feasible technology, but becomes a goal and symbol for new in vivo capsule-based technology development. It is that vision of improving diagnostic and scientific and engineering technology for improving human health that is embodied within the generic Capsules A and B, and their hybrids (AB) and having the world scientific community contribute thereto.

Perhaps the ultimate greatest current benefit may be a result of on-board electronics, which creates five basic options: a) actively on demand, or passively collect samples, b) make measurements, process the data, and either store it or transmit it in real time, or c) make calculations from the measurements and take action based upon the calculated results, or d) make injections or releases based upon preprogrammed time or location parameters, or most importantly, e) take measurements, either of the chyme or other lower intestinal tract substances, or from the human body responses, such as pulse rate or an autoimmune response, make calculations on those data, make decisions based upon those data, and execute preprogrammed commands based upon values of said processed data. This interactive capability of Capsule B is huge, because it provides among many options, to apply medication or any chemical for any purpose at an exact location at an exact time, based upon for example, an immediate feedback response from the human body, or other conditions existing within the intestinal tract.

3. Capsules A and B as Multiple Evolutionary Components

The capabilities of the sampling and in vivo measuring capsules, A and B, and their hybrids AB, of necessity must conform to the demands and characteristics of the system being researched and investigated for whatever purpose. It is important at this point to digress momentarily to discuss the nature of this system to be investigated in order to give meaning and purpose to the various designs of capsules A, B, and AB.

The Human Intestinal Tract to be Investigated

The entire human food ingestion-digestion tract may be regarded as having such major components as the mouth, esophagus, stomach, small intestine and large intestine, each having major distinct roles. The conditions within each vary widely from a food processing or an instrumentation perspective. There are also smaller scale functioning components within each of these, which need monitoring and modeling, as well as, the progressive changes to the food products as it passes through each major component. For simplicity at this point, consider the cross section at any point along the total ingestion-intestinal tract as a function of the length x, where x=0 at mouth, and x=L at anus/rectum, and at each cross section the shape is a function of radius R and angle theta. Just consider the gut for simplicity now, as having an elliptical or circular tubular cross section through which liquids, solids and gases pass as a biochemical reacting slurry in varying ratios. The cross sectional velocity, as in any tubular fluid flow, has some form of a parabolic profile, wherein the velocity is maximum at the center and zero at the outer boundary wall, i.e. $V_{R=0}$ at center of gut is max, and $V_{R=RW}$ at the outer wall is zero. Also, at the vicinity of the outer wall there is a boundary layer across which the velocity normally goes to zero in a closed impermeable tube. However, in the human gut, mass and energy pass through the permeable wall eventually into the bloodstream via ville, and other means in the colon, where liquids are extracted. This "boundary layer" according to this author's discovery plays a major role in the digestion system, and even more importantly, the source of major diseases.

Therefore, any sampling capsule must accommodate these conditions and all phenomena to be investigated therein, ranging from the processes, the sampling substances and their phases, to the microbes therein as functions of radius, angle theta, and x. For this reason, the capsules A are really $A_{i,j}$ where i=1 to m, to reflect different capsule designs, and j=1 to n, to reflect the diseases or phenomena to be specifically investigated. The j=1 category is for general purpose, comprehensive sampling for any/all purposes ranging from research, to patient testing, and education. For purposes of illustration, Capsule $A_{1,1}$ had a specific, unique design to sample within the boundary layer adjacent to the outer wall of the intestinal tract. Now, Capsule $A_{2,1}$ is of another distinct design to sample for general purposes, but from the center of the intestinal tract, wherein instead of a thin belt collecting samples from the outer peripheral slit in the capsule housing, the sampling intake is through a port of selectable diameter D in the center of the capsule. Also, in this unique design, substances and microbes simultaneously are pulled into the port by a helical auger type of central construction that gives positive displacement at a prescribed design rate, to not only force sampling, but can also give a self-propulsive characteristic to the capsule for the excess substances passed through and not retained as samples, wherein the design ratio of sample volume/extruded through volume can go from a small fraction, e.g. 0.1 where propulsion force is maximum, to 1.0 wherein all intake sample is saved and the propulsive force equals zero. The samples are stored within Capsule $A_{2,1}$ to preserve their identity and integrity, either on a similar belt with pockets and a sealing cover as in $A_{1,1}$, or in single or multiple impermeable storage tubes as a result of the auger forcing the samples through in a positive displacement method, depending upon the specific objectives, including sampling of different phases and determining phase ratios, for example. This will be discussed later as an example in the Claims under the Protocol Claims. In summary, capsules may now be classified and referred to as either $A_{i,j}$ or $B_{i,j}$, or $AB_{i,j}$.

4. Capsule Incubator and Manipulator (Also Evolutionary Compatible with Capsule Designs)

The system integrally designed Capsule Incubator and Manipulator machine performs a series of functions, including preserving the integrity of the in-vivo obtained conditions until such time and under said conditions each and every obtained sample can be either: stored, transported or tested and analyzed. The Manipulator positions the Capsule, constrains it, removes the collected samples cartridge and then can either insert it into a similar sealed capsule for archive storage or for transport, or insert it into a second platform testing cartridge, where the sample spools are removed and placed into the traverse testing table with its own indexing and motor drive identical dimensionally and characteristically to the sample collection cartridge drive and indexing mechanisms. This sample spools transfer is all done robotically, or technician remote assisted, under a "bell jar" in-vivo simulated and controlled environment, whereupon both the samples and technicians are protected in conformance with biological specimen handling protocols. The samples once placed in the portable traversing-indexing and forward/reverse spooling cartridge are now ready for temporary storage in an in-vivo simulated environment, or for immediate testing and characterization.

5. Analyzer

A comprehensive system of probes and instrumentation systems are both specifically designed, and in some cases selected off the shelf, to measure the chemical composition and characteristics of substances. The probes and data acquisition system are also integrally designed to be compatible dimensionally and logistically with the samples collection and temporary storage system. In particular, special chemicals will be searched for as toxins to the human immune system, and the environment in which they were generated will be known, and through reverse energetics calculations, how they were created can be determined. Likewise, the same exact sample can be non-destructively examined microscopically to identify and characterize microbes existing at each instant and position and associated with the chemical compositions at the same exact position in the intestinal tract. Thus, the role of microbes can be ascertained. All data are recorded on computer-based data acquisition systems in data bases and spreadsheet formats suitable for comprehensive statistical, graphical and other analysis methods, much of which will be automatically performed, included modeling in simulated real time, and 3-D computer graphics models of the processes taking place within and along entire length L of the intestinal tract.

6. Computer-Based Data Acquisition, Reduction, Analysis, and Display System (CBDARADS)

This system performs a variety of functions. All data from a wide variety of instruments in diverse formats must first be converted into a single compatible format for acceptance and manipulation by the system, so that it can then be processed. After appropriate electronic signal conditioning and standardized formatting, the output data from various instruments are converted first into SI units so that all future calculations will be simplified. Data are compiled into data bases and spreadsheets for viewing and designing further graphical displays which are then incorporated into the auto-processing/display mode to constitute in some applications, real-time data diagnostic and interpretation, and other uses.

7. Applications of the Invented System to Patients

Patient Preparation and Testing Protocols

Protocols are designed by a multidisciplinary team of physicians, and research scientists and engineers for designing the entire patient preparation and testing process beginning with:

a) patient physician recommendations to accommodate the peculiarities and specific conditions of the patient to be tested and evaluated based upon symptoms as diagnosed by all attending physician(s), using other existing conventional medical diagnostic methods and equipment as guidance;

b) patient physician and researchers specification of diet or other preconditioning;

c) specific samples, sizes, quantity, to be collected to focus upon specific hypotheses, diseases, or other agenda;

d) testing and diagnoses methodologies for the samples to focus upon specific hypotheses, diseases, or agenda;

e) specific data presentation in specific computer graphic and other formats; and f) creation of individual patient intestinal flora profiles with intent to conduct further research to link said profiles or specific strains of bacteria, or combinations thereof, to patient existing diseases, or apriori prediction of risk for onset of specific future diseases.

8. Applications to Advancing Knowledge and Understanding of Human Gut

Many disciplines and branches of science and engineering have a vested interest in the processes taking place in the human gut, and as a result, the information that can be generated by this invented system. It is therefore anticipated that many research projects from a multitude of disciplines beyond the immediate medical sciences will be initiated, once this capability is available to the broad research community.

Although these data will be made available to multi-discipline specialists throughout the medical profession, it is anticipated that groups of diverse multi-discipline scientists and engineers will develop many special tests, procedures and protocols to render the total process most effective and applicable to the most serious diseases and illnesses threatening human health that may have an origin in the human gut.

9. Applications to Advancing Knowledge, Science and Technology in Various Fields The wealth of data and information collected from this human gut research and diagnostic system (RDS) can actually be used in many macro and micro branches of science, engineering and technology. As generally regarded as the most perfect machine, the human body processes often have applications that can be simulated and applied in other man made machines and technologies. One interesting aspect that can be investigated by the herein invented RDS is the energetics of the rapid and large volumes of intestinal tract gas production as a result of a patient ingesting wheat products, and having some "gluten sensitivity". Are these same "unknown, un-identified, and un-characterized" bacteria strains and colonies that are so capable of converting so efficiently gluten or other proteins, or other biomaterials into gaseous products also useful in an external, commercial digester? These bacteria and their byproducts with the other substances need to be captured and held in captivity suitable for extensive research. This is only one of many readily identifiable possibilities for uses of said samples, data and information generated from the RDS. The spin off technologies of developing additional micro-miniature sensors and transducers should also be useful in many other applications.

10. Research and Medical Profession Protocols

A sample of substances or microbes, or set of elaborate data is only as good as the peripheral information of pre-existing conditions under which the information were obtained. Therefore, meaningful application of this RDS, of necessity, incorporates instruction sets under which it should be used, and some prior knowledge of the subject to which it is applied. Otherwise, interpretation of the data is not realistically possible. Also, before prescribing any medication or whatever following the obtaining of samples and data from the RDS, medical professionals must know the initial conditions anyway, and furthermore as a means of later evaluating effects after follow up uses of the RDS. Although such protocols would be necessary for patient applications, they are just as important in any research project as a matter of competent research methodology. As a result, and to also discourage and help avoid misapplication of the RDS, such protocols are considered part and parcel to the subject invention. This is also in part what led to the necessity of the unique RDS feature and method of simultaneously capturing all substances and the associated microbes at the same exact location and instant in time. There are also external, extraneous variables considered important to control as part of said protocols.

11. Analysis and Interpretation of Data

Although presentation of the data includes every conceivable manner of illustration to reveal all possible features as clearly and efficiently as possible, interpretation is the most important phase. In fact, interpretation may continue by case studies long after initial data sets are thoroughly displayed and analyzed for immediate decision making. Interpretation must also be done by a multi-disciplinary team, and standard formats will be introduced and developed as numerous data sets have been thoroughly analyzed by such teams.

Important Clarification Points for RDS

The present invention is a comprehensive method and process, complete with application protocols, and a unique apparatus and comprehensive, integrally-designed Research and Diagnostic System (RDS) with integrally designed components, for simultaneously obtaining samples of partially through completely digested food products or matter and the associated microbes, at the same exact location and time, along the entire human or other animal intestinal tract originating in the mouth and terminating at the end of the colon or anus. The present invention is able to be used is for obtaining samples of partially digested food products or digestive tract matter, as well as, microbes along the entire human, or other animal, gastrointestinal tract originating in the mouth and terminating at the end of the colon or anus. It should be noted that the present invention is able to specifically target either type of sample exclusively.

The present invention additionally provides a unique apparatus with integrally designed comp for use with a comprehensive method and process, complete with application protocols integrally-designed Research and Diagnostic System (RDS). The system of apparatuses of the present invention comprises an electrical mechanical Device, an Capsule Incubator and Manipulator, an Analyzer, and an Computer-Based Data Acquisition, Reduction, Analysis, and Display System (CBDARADS).

The electromechanical device of the present invention, hereinafter referred to as a capsule, is designed, fabricated, and administered for ingestion by human research subjects or patients, in order to collect, store, and preserve, collected sample integrity and in-vivo environmental conditions from beginning to end of the intestinal tract, and beyond for chemical and biological testing when placed in a simulation incubator. The capsule comprises a specially designed housing, a thin film belt, and an electro-mechanical belt drive mechanism.

In current embodiment of the present invention, the capsule comprises a specially designed housing. The specially designed housing comprises special curvatures of defined algebraic functions, a porous permeable grid, and guidance rails. The special curvatures of defined algebraic functions serve a variety of purposes including ease of passage through intestinal tract, relative velocity of passage to that of food products, and position relative to intestine walls. The porous, permeable grid that readily allows processed food products and microbes to migrate through, yet safely separates it from the sidewalls of intestines. The guidance rails are for precisely locating and positioning of said capsule with sample collection belt with respect to the grid covered open window slot that receives sample products. Additionally, the specially designed housing is opaque to all wavelengths of radiation comparable to the human body shield that would be harmful to microbes or biochemical reaction or degradation processes. Furthermore, the specially designed housing is inert to contents of the gastro juices or intestinal tract contents and human immune system. Moreover, the specially designed housing provides ease of assembly, sealing, and recovery of sample collection cartridge.

In the current embodiment of the present invention, the thin film belt comprises imprinted/indented pockets. The imprinted/indented pockets comprise special patterns and special designed pocket and a thin film hermetic seal. The special patterns and special designed pocket s shapes, sizes and distributions as function of length, for sample collection to constitute a continuous sampling process at each point along the entire length L of the intestinal tract. The thing hermetic seal is applied to permanently cover the collection sample belt and its pockets to prevent sample contamination from one position to any other along the entire length L. The imprinted/indented pockets are positioned along the thin film belt, wherein the imprinted/indented pockets at the beginning and end of the thin film belt seal slit in the capsule housing to preserve initial sterile or post collection conditions of collected samples until such time the cartridge is removed from said housing. The imprinted/indented pockets being utilized for collected sample storage constituting an indexed collection method collecting up to 15,000 samples from beginning to end of intestinal tract.

In the current embodiment of the present invention the electro-mechanical belt drive mechanism comprises a power source, a drive train, and an associated removable cartridge assembly. The thin film belt being easily removed, either robotically or via technician manual remote assist, under preserved environmental conditions and conveyed into another storage capsule housing, or transferred to an indexing table for samples testing, or any other testing apparatus. Additionally, the electro-mechanical belt drive mechanism has programmable revolutions per minute to accommodate belt traveling speed and thus sampling rate or frequency as a function of x, and a triggered power shut off switch to disengage and stop the belt when the end of the sampling belt is reached. Furthermore, the electro-mechanical belt drive mechanism being contained in a removable cartridge may be of any other design that accesses intestine contents, samples them, and appropriately stores them all of which is accomplished by a similar cartridge subsystem herein exemplified, since subject sample products vary from a slurry, such as the fluidic chyme in the duodenum, to solidified stools in the lower colon, so must the capabilities of the capsules.

In the current embodiment of the present invention, a version of the capsule, hereinafter referred to as capsule $B_{i,j}$ unless otherwise specified, is an all-in-one tool, with immediate monitoring and administration functions allowing the deliverability and release of medication or other substances to a specific location or at a specific time, or both independently, and interactively based upon measured values either from the intestinal substances, or conditions, or active or feedback responses measured from various human body organs or systems.

In current embodiment of the present invention, a version of the capsule, hereinafter referred to as capsule $AB_{i,j}$ unless otherwise specified, is capable of collecting some gaseous, liquid, or solid samples for later analysis, while simultaneously making some in vivo measurements resulting in combined and new capabilities of simultaneous quantitative measurements and samples collection utilizing Capsule based technology.

In the current embodiment of the present invention, the capsule incubator and manipulator provides for and facilitates the handling and maintenance of in vivo conditions, and retrieval of said taken samples while maintaining in vivo conditions, and placing said collected samples into another cartridge for storage or transport, or retrieving said samples from said cartridge and placing them with their container belt or tubular belt onto another indexing type of platform suitable for transport to and manipulation for use by an assortment of instrumentation and testing probes and a large variety of other laboratory instruments.

In the current embodiment of the present invention the analyzer comprises an assortment of instrumentation and testing probes and a large variety of other laboratory instruments and testing equipment including spectrometers, chromatographs, microscopes and SEMs, and numerous other equipment for determining mechanical, chemical, physical, biological, bio-energetic, electrical, fluid, thermal, and other properties of intestinal substances, and comprehensive microbiological testing, evaluation, classification, and characterization of known and unknown microbe strains and species according to Phylogeny Tree of living organisms, as well as an indexing table that provides each sample access to the numerous probes, which consist of newly designed and developed probes and interface devices and modified instruments suitable for interfacing with the intestinal sample indent storage pockets within the sample belts or the tubular vessels.

In the current embodiment of the present invention, the CBDARADS comprises a unique construction, assembly and combination of instrumentation, computer-based hardware and software systems, with unique data processing and display features, and capabilities of feedback when queried, or used in interactive patient applications developed for special requirements of RDS.

The present invention is a comprehensive method and process, complete with application protocols for a human intestinal tract Research and Diagnostic System (RDS) capable of generating sufficient data and information for constructing ultimately a comprehensive engineering simulation model of the human gut, comprised of sub-system models, including data suitable for determining coefficients of a variety of equations used to describe and simulate the flow, chemical, endothermic/exothermic, biochemical, aerobic/anaerobic, bioenergetics, microbiological, and many other aspects and characteristics of a functioning human gut. The method of the present invention is provided with sub-function models, master combined, and comprehensive models intended to elevate multiple macro and micro functions of the human gut, and their interactions, to various levels of abstraction for computer software simulation purposes, and ultimately to be used in conjunction with real, specific-patient data, for the evaluation of disease cause and effect relationships, and predicted, projected and simulated apriori impact evaluations of various medications and diets, including creation and development of new medications and diets, as a means of expediting improvement of human health, and disease prevention. The comprehensive method and process of the present invention uses the RDS to create a human gut flora profile, wherein said profile may lead to explanation of existing diseases, or apriori of future onset of specific diseases. The present invention is able to correlate specific flora strains or combinations thereof, as may be related to certain locations, with existing or future onset of specific diseases. The present invention is able to deliver custom medications/antibiotics by way of the RDS to certain location with existing or future onset of specific diseases, for inoculation and prevention. Furthermore, in the present invention, the RDS is applied to other animals, and used to learn of their gut system processes and functions, as well as, diagnostic purposes for their diseases and health problems, while allowing the subject system to be further tested and developed and applied safely in other animals while being perfected and extensively development for human applications. Moreover, the RDS can be appropriately adapted with lower cost for use as an extremely valuable multi-disciplinary teaching tool in medical and other schools as dietary and food research, and, of course, many other diseases not typically associated with the intestinal tract.

Additionally the present invention is an experimental Celiac disease protocol for the application of a Research and Diagnostic System (RDS) for use with human subjects in order to establish accurate cause and effect relationships in diagnosis of celiac and related disease progression in phases over a period of time as well as rates of severity. The present invention provides a system to investigate, wherein said investigated system such as the human, urinary and intestinal tracts, auto-immune, cardiovascular and other systems. The present invention provides a controlled environment for investigated systems, wherein the initial and current conditions under which the RDS is administered are maintained to have the exact same daily diet, level of exercise and other factors as constants for at least three consecutive days in order to establish a steady state conditions. The present invention provides an RDS for an investigated system, wherein the RDS is administered in similar to currently available capsulated mendicants. The present invention initiates a first cycle of RDS administration to investigated system on fourth consecutive day while maintaining same exact diet and routines as prior several days, wherein a cycle of RDS administration commences upon ingestion of RDS by investigated system and concluded upon expulsion/recovery of RDS from investigated system. The present invention then initiates a second cycle of RDS administration to investigated system upon completion of first cycle of RDS administration while maintaining same exact diet and routines as prior several days. After which the present invention initiates a third cycle of RDS administration to investigated system upon completion of second cycle of RDS administration while maintaining same exact diet and routines as prior several days. At which point the present invention performs tests and analysis of data for intestinal flora profile consistencies and similarities in terms of strains/species and populations, as well as, chemical substances and concentrations profiles, and create a statistical original condition for the first cycle, the second cycle, and third cycle of RDS administration.

The present invention then alters the controlled environment by way of changing investigated systems diet to gluten free diet while maintaining same routines for a period of two weeks. Upon altering the controlled environment the present invention initiates a first cycle of gluten-free RDS administration to investigated system at beginning of third week while maintaining same exact Gluten-free diet and routines as prior several days. At which point the present invention initiates a second cycle of gluten-free RDS administration to investigated system upon completion of first cycle of gluten-free RDS administration while maintaining same exact Gluten-free diet and routines as prior several days. After which, the present invention initiate a second cycle of gluten-free RDS administration to investigated system upon completion of first cycle of gluten-free RDS administration while maintaining same exact Gluten-free diet and routines as prior several days. The present invention initiates a third cycle of gluten-free RDS administration to investigated system upon completion of second cycle of gluten-free RDS administration while maintaining same exact Gluten-free diet and routines as prior several days. With all three cycles administered to completion the present invention performs tests and analysis of data for intestinal flora profile consistencies and similarities in terms of strains/species and populations, as well as constructing delta gut flora profiles, and delta substances profiles, by statistically significantly differentiating between the profiles the first cycle, the second cycle, and third cycle of Gluten-free RDS administration.

The present invention initiates analysis of the collected data by observing the differential different strains/species and relative populations of bacteria as a function of x and the differential different chemical compounds and concentrations as a function of x. the present invention then commences interpreting data of the differential different strains/species collected for presence of the particular strains of bacteria or "gluten loving bacteria" as well as, their relative position as functions of in order to target for control or elimination. Furthermore the present invention simultaneously commences interpreting data of the differential different chemical substances collected for presence of chemical substances created by the combined biochemical reactions and the bacteria processed food substances, for chemical substances of concern. With data collection and analysis completed the present invention creates a 3-D graphical illustration of collected and interpreted data. The invention then stores the data in databases and spread sheets for facilitated access by multidisciplinary groups for research purposes and various uses. by the actions performed through these steps, users are able to gain greater insight into the digestive tract functions, processes, and resulting conditions threatening human health can be concluded, modeled and applied.

In the current embodiment of the experimental Celiac disease protocol for the application of a Research and Diagnostic System (RDS) for use with human subjects, the aforementioned RDS tests, and protocols as illustrated, provide for, but not limited to, the detection of and determination of characteristics of specific bacteria responsible for gluten related illnesses and diseases. Additionally, the resulting problematic chemical substances are identified and characterized. Furthermore, the said RDS and above illustrated processes can be applied to other intestinal tract disorders, and diseases originating in the gut and lead to cures for many other diseases within other anatomical systems.

In an embodiment of the present invention the RDS has the ability to providing to deliver and release medication or other substances to a specific location or at a specific time, or both independently, and interactively based upon measured values either from the intestinal substances, or conditions, as well as active or feedback responses measured from various human body organs or systems. The present invention accomplishes this by administering RDS containing medication or other substances to investigated system. The present invention then delivers RDS to a specific location or at a specific time, or both independently, and interactively, wherein the specific point of interest is any point of interest within the investigated system. upon delivering the RDS to the specific the location or at a specific time, the present invention then releases the medication or other substances from RDS based upon a pre-programmed criteria such as measured values either from the intestinal substances, or conditions, as well as active or feedback responses measured from various human body organs or systems, wherein the specific measurements include presence of chemical substances or microbes, or the results of any effects they may have had that resulted in any specific condition with specified parameters within the investigated system. The present invention then measures immediate effects of the released medication or other substance from the RDS at the specific location or at the specific time on the chemical substances, microbes, any other hypothesized phenomena or variable of interest, as well as any specific human autoimmune responses as reflected by preprogrammed measurement criteria present within the investigated system.

In an embodiment of the present invention the ability of the RDS to repeat tests and evaluations within the intestinal tract immediately caused by some diet or medication administration, or any perceived changes within the body that would warrant taking another capsule. Thus, within the time it takes for a test sampling capsule to be evaluated after passing, and any medication is administered, another capsule can be taken and the immediate change in the unique individual flora and biochemical substances profiles can be determined. This provides evaluation of immediate, or later, effectiveness, or positive or negative impacts of any drug, as well as provides insightful data to facilitate the immediate improvement and development of drugs, all based upon factual data. Furthermore, the present invention is able to reduce cycle time for new drugs development, testing, approval, and patient applications, such that specific capabilities have many research, legal, educational, clinical, technology development, and other applications to advance patient remedies and medical science and technology. Moreover, this embodiment of the present invention can provide a new system that allows, facilitates, and provides for merging of micro and macro data, and sciences, engineering, and technologies integration and simultaneous development for the human gut.

In summary, the RDS and all of the associated testing and protocols should confirm the old adage that, "A person's body is what they eat", but with a corollary phrase at the end of the sentence: "and in conjunction with the individual's unique gut flora profile, revealing of the predictable diseases it will suffer". This is why some physicians believe in occasional "cleansing" of the gut. The only problem is that the "cleansing" act is not defined or understood and the results are unknown, at both the micro and macro levels. This invention can solve most of this mystery and dilemma.

Although the invention has been explained in relation to its preferred embodiment, it is to be understood that many other possible modifications and variations can be made without departing from the spirit and scope of the invention as hereinafter claimed.

What is claimed is:

1. A device for acquiring samples of matter along an intestinal track of a user, the device comprising:
    a capsule configured to be swallowed and passed through the intestinal track, the capsule including;
        a housing defining an opening adapted to allow the samples of matter to pass into the housing,
        a belt disposed within the housing and defining a plurality of indentations, each of the indentations having a volume configured to collect the samples of matter, and
        a motor disposed within the housing and configured to drive the belt for collecting the samples of matter at a predetermined rate as the capsule passes through the intestinal track.

2. The device as claimed in claim 1, the device further comprising a receiver, wherein the receiver is configured to monitor the process of the capsule by active telemetry.

3. The device as claimed in claim 1, the capsule further comprising a battery, wherein the battery is configured to power the motor.

4. The device as claimed in claim 1, wherein the batter is a wafer battery.

5. The device as claimed in claim 1, wherein the housing is opaque to light waves for protection of collected samples of matter.

6. The device as claimed in claim 1, wherein the capsule housing includes multiple ends wherein each end is attached by a thread and sealed with an O-ring.

7. The device as claimed in claim 1, the capsule further comprising a mesh attached to the capsule housing configured to prevent the belt from touching the lining, epithelium, villi or obtrusive parts of the intestines.

8. The device as claimed in claim 1, the capsule further comprising a spool having a hermetically sealing film; wherein the spool and film are configured encapsulate the matter samples by attaching the film to the belt after the belt has collected the matter samples.

9. A method for collecting for acquiring samples of matter from along an intestinal track of a user, the method comprising the steps of:
    providing a capsule configured to be swallowed and passed through the intestinal track, the capsule including;
        a housing defining an opening adapted to allow the samples of matter to pass into the housing,
        a belt disposed within the housing and defining a plurality of indentations, each of the indentations having a volume configured to collect the samples of matter, and
        a motor disposed within the housing and configured to drive the belt for collecting the samples of matter at a predetermined rate as the capsule passes through the intestinal track,
    inserting the capsule into the gastrointestinal track; and
    analyzing the collected samples of matter collected by the capsule to determine the composition of the intestinal track.

10. The method as claimed in claim 9, further comprising the step of monitoring or tracking the position of the capsule by x-ray, magnetic resonance imaging (MRI), or active telemetry.

11. The method as claimed in claim 9, wherein the step of analyzing the collected samples of matter further includes identifying and characterizing microbes in collected in the indentations.

\* \* \* \* \*